United States Patent
Watanabe

[11] Patent Number: 5,482,599
[45] Date of Patent: Jan. 9, 1996

[54] PHOTOCHEMICAL METHOD FOR CONVERTING CARBON DIOXIDE GAS TO ORGANIC SUBSTANCES

[75] Inventor: Masao Watanabe, Saitama, Japan

[73] Assignee: Advantest Corporation, Tokyo, Japan

[21] Appl. No.: 196,113

[22] PCT Filed: Jun. 15, 1993

[86] PCT No.: PCT/JP93/00799

§ 371 Date: May 5, 1994

§ 102(e) Date: May 5, 1994

[30] Foreign Application Priority Data

Jun. 17, 1992 [JP] Japan .................................. 4-158053

[51] Int. Cl.$^6$ ...................................................... C07C 1/00
[52] U.S. Cl. ........................ 204/157.15; 204/157.6; 204/157.9
[58] Field of Search ............................ 204/157.15, 157.6, 204/157.9

[56] References Cited

FOREIGN PATENT DOCUMENTS

| 55-105625 | 8/1980 | Japan. |
|---|---|---|
| 58-40148 | 3/1983 | Japan. |
| 4-36249 | 2/1992 | Japan. |
| 4-45853 | 2/1992 | Japan. |
| 4-59037 | 2/1992 | Japan. |
| 4-122453 | 4/1992 | Japan. |

OTHER PUBLICATIONS

Aurian–Blajeni et al., Photoreduction of Carbon Dioxide and Water into Formaldehyde and Methanol on Semiconductor Material, Solar Energy, vol. 25 (1980), pp. 165–170.

Primary Examiner—John Niebling
Assistant Examiner—Edna Wong
Attorney, Agent, or Firm—Staas & Halsey

[57] ABSTRACT

Fine particles of ZnO are subjected to heat treatment at 400° C. for four hours under vacuum to activate the surfaces thereof, the activated ZnO particles are brought into contact with saturated water vapor, and then subjected to irradiation by visible light under an atmosphere of $CO_2$ gas or $CO_2/H_2O$ mixture gas at 5° C. and 33 atm, that is, under the clathrate hydrate phase forming conditions.

4 Claims, 7 Drawing Sheets

PHOTOCHEMICAL METHOD FOR CONVERTING CARBON DIOXIDE GAS TO ORGANIC SUBSTANCES

FIELD OF THE INVENTION

This invention relates to a photochemical method for converting carbon dioxide gas to organic substances such as methanol using visible light such as solar light.

DESCRIPTION OF THE RELATED ART

It has been advocated that the emission of carbon dioxide gas to the atmosphere be limited, and concurrently therewith, research on the reduction and conversion of $CO_2$ molecules have begun to be developed rapidly. The current trend of such researches is towards catalytic reactions, organic photosynthetic reactions, electrochemical reactions, photoelectrochemical reactions, and the like for decomposing $CO_2$ molecules or decomposing $CO_2$ molecules while at the same time incorporating decomposed molecules into organic molecules. Known as one of such reactions is the Fischer-Tropsch reaction comprising decomposing carbon dioxide gas into carbon monoxide and oxygen, followed by subjecting the resulting carbon monoxide to a catalytic reaction with hydrogen to produce hydrocarbon having a higher molecular weight. However, this process requires a large quantity of hydrogen gas, so that the resulting hydrocarbon products will be too expensive to be put to practical use in an industrial application. Furthermore, it requires highly safe and hence expensive facilities in consideration of the possibility of explosion of hydrogen gas.

Besides the foregoing, studies have been conducted on catalytic reactions for synthesizing methanol or methane from $CO_2$ and $H_2O$ molecules, but none of them have been found advantageous in that they use costly $H_2$ as a raw material.

Studies are still in the early stage on the photosynthetic reactions (relying on light and catalysts) which are considered the simplest, as represented by the following formula (1):

$$CO_2+H_2O \rightarrow CH_3OH+(3/2)O_2-63 \text{Kcal/mol} \qquad (1)$$

Fujishima et al deal with this type of photosynthetic reaction using various semiconductors as a catalyst in the "Nature" Vol. 277, February 1979, pp 637–638. Disclosed in this paper is the process of converting carbon dioxide to methanol using powders of $TiO_2$, ZnO, CdS, GaP, Sic, $WO_3$ or the like, for example as a semiconductor catalyst and irradiating the catalyst with ultraviolet radiation from a xenon lamp. However, the conversion efficiency has proved so poor as to be unsuitable for practical application. Moreover, the wavelength components taking part in the photosynthesis are ultraviolet light which is little contained in the solar radiation reaching the surface of the earth as it attenuates before reaching the surface. Consequently, the use of a source of ultraviolet light such as a xenon lamp is essentially required, making the process far from practical and economical.

In view of the foregoing, the Japanese Patent Application No. 2-144227 proposed a photosynthetic process comprising heating metallic oxide to activate it so as to produce free electrons and free holes locally on the surface thereof, and applying $CO_2$ and $H_2O$ gases to this metallic oxide while irradiating the metallic oxide with visible light energy to photosynthesize organic substances. More specifically, fine particles of ZnO (zinc oxide) are heated under vacuum to eliminate relatively many of O atoms bonded to Zn near the surfaces of the fine particles, and to create locally on the particle surfaces a number of regions where imperfect ZnO lattices with excessive $Zn^{++}$ (positive ions) are generated and a number of regions where the elimination of O atoms scarcely occurs.

Figure 7:
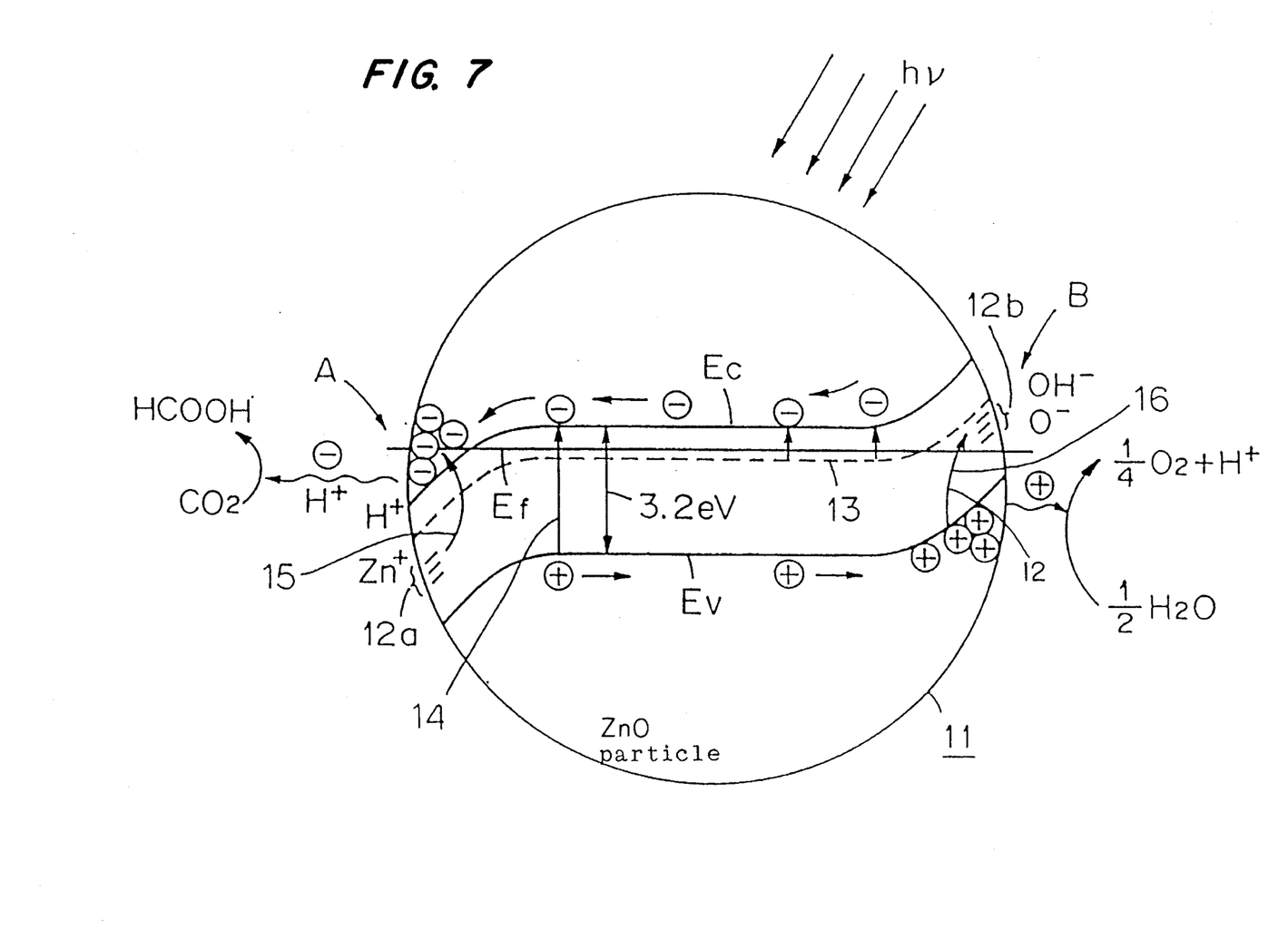
FIG. 7 a diagrammatical view illustrating the band structure of ZnO fine particle, the process of electrons and holes being excited on the surface of ZnO fine particle by irradiation by visible light, and the decomposing reactions of H₂O molecules and CO₂ molecules.

As seen in FIG. 7 illustrating the surface energy band structure of the ZnO particle, in the region (A) (the lefthand surface region of the particle 11) where numerous O atoms have been eliminated, positive ions ($Zn^{++}$) become excessive at the surface layer where the energy band is bent downwardly, and free electrons will accumulate or build up at the downwardly bent portion of the band, resulting in generation of surface conductance. Also present on the surface are protons $H^+$ which have been produced by decomposition of water. In FIG. 7, $E_v$, $E_f$ and $E_c$ stand for the energy level of the valence band, the Fermi energy level, and the energy level of the conduction band, respectively. On the other hand, in the region (B) (the righthand surface region of the particle 11) where the elimination of O atoms scarcely has occurred, the energy band is bent upwardly at the surface layer due to the presence of $OH^-$ and $O^-$ formed by the water and oxygen in the atmospheric air having been adsorbed onto the particle surface and decomposed. As a result, holes will build up or accumulate in the surface. Thus, the free electron build-up regions (A) and the free hole build-up regions (B) are distributed dispersedly over the surface of the ZnO particle.

Another important effect of activating ZnO by heat treatment is that impurities contained in zinc oxide will build up on the surface layer of the zinc oxide due to the heat treatment to constitute impurity levels 12a, 12b in the forbidden band, thereby enabling excitation of electrons and holes by visible light, and hence photosynthesis as will be described hereinbelow.

The width (difference between $E_v$ and $E_c$) of the forbidden band of ZnO is 3.2 eV. It is thus required to provide irradiation by light having an energy hv greater than 3.2 eV, that is, ultraviolet light having a wavelength shorter than 389 nm in order to produce pairs of free electrons and holes by exciting electrons up to the conduction band across the forbidden band from the valence band as indicated by the arrow 14. However, as shown in the surface region (A) of the fine particle 11 of activated ZnO, the impurity level 12a, being lower than the Fermi level $E_f$, acts as a donor level, from which electrons may be excited by photoexcitation up to the energy level $E_c$ of the conduction band as indicated by the arrow 15 to generate free electrons.

On the other hand, the impurity level 12b as shown in the surface region (B) of the ZnO fine particle 11, being higher than the Fermi level $E_f$, acts as an acceptor level, so that free electrons may be produced by photoexciting electrons from the valence band up to the acceptor level 12b as indicated by the arrow 12. That is, by heat treating ZnO it is possible to form free electron build-up regions (A) and free hole build-up regions (B) over the surface of the ZnO particle, to bend the energy band, and further to form impurity levels 12a and 12b acting as donor and acceptor levels, respectively, whereby free electrons may be produced by exciting electrons with visible light. Further, while ZnO possesses the property of n-type semiconductor due to the lattice defect and a donor level as shown in broken lines 13, they do not contribute to the surface conductance.

In the free hole build-up regions (B) of the surface of ZnO, the holes will move to the adsorbed $H_2O$ molecules to thereby generate $2H^+$ as represented by the following formula (2):

$$H_2O + 2(+) \rightarrow (½)O_2 + 2H^+ \quad (2)$$

The protons H⁺ produced by this reaction will move to the electron build-up regions (A) by surface diffusion. On the other hand, in the electron build-up regions (A) of the surface of ZnO, the produced electrons and protons will move to CO₂ to thereby generate formic acid as represented by the following formula (3):

$$CO_2 + 2H^+ + 2(-) \rightarrow HCOOH \quad (3)$$

Following this reaction, the movement of electrons and protons will be further repeated to produce HCOOH. And it is considered that the following reactions will proceed:

$$HCOOH + 2H^+ + 2(-) \longrightarrow HCHO + H_2O \quad (4)$$

$$HCHO + 2H^+ + 2(-) \longrightarrow CH_3OH \quad (5)$$

$$\longrightarrow CH_4 + (1/2)O_2 \quad (6)$$

Thus, as a whole the photosynthetic reaction as represented by the formula (1) is accomplished.

By the use of surface activated ZnO as a catalyst, water and carbon dioxide may be converted to organic substances by reacting them with each other by means of solar light under normal temperature and pressure conditions. That is, no costly ultraviolet light is required. However, this process had the disadvantage that the efficiency in conversion to organic substances is as low as about 0.1%.

It is an object of the invention to provide a process of converting carbon dioxide gas to organic substances, comprising subjecting the carbon dioxide gas and water to photochemical reaction with a high efficiency using visible light with a surface activated metallic oxide as a catalyst.

SUMMARY OF THE INVENTION

According to a first aspect of this invention, a metallic oxide is heated to activate the surface thereof, water, and carbon dioxide gas are applied to the surface activated metallic oxide while the metallic oxide is irradiated with visible light, whereby the carbon dioxide gas is converted to organic substances at a temperature of 0° to 10° C. and a pressure of 30 to 40 atm.

According to a second aspect of this invention, a metallic oxide is heated to activate the surface thereof, a clathrate hydrate phase of water is formed so as to be in contact with the surface activated metallic oxide, carbon dioxide gas is introduced into the clathrate hydrate phase, and the surface activated metallic oxide is irradiated with visible light, whereby the carbon dioxide gas is converted to organic substances.

It is known that the reactant water will solidify under the conditions of a temperature below 10° C. and a pressure of 30 to 40 atm to form a structure consisting of interlinked thirty-two sided polyhedric cages and thirty-four sided polyhedric cages, that is, a so-called clathrate hydrate phase. CO₂ molecules cannot move within a usual ice, but in the clathrate hydrate phase, they are situated centrally in the cages and yet can move fairly freely. Accordingly, if carbon monoxide gas is applied to a clathrate hydrate phase formed on the surface of surface activated metallic oxide, the CO₂ molecules will move in the clathrate hydrate phase and reach the surface of the metallic oxide which is a site of reaction, so that the densities of the H₂O and CO₂ molecules are increased and the interaction therebetween are intensified. It is thus considered that the photosurface reaction according to the formula (1) is accelerated to increase the quantity of organic substances produced.

DETAILED DESCRIPTION OF THE PREFERRED EMBODIMENT

Figure 1:
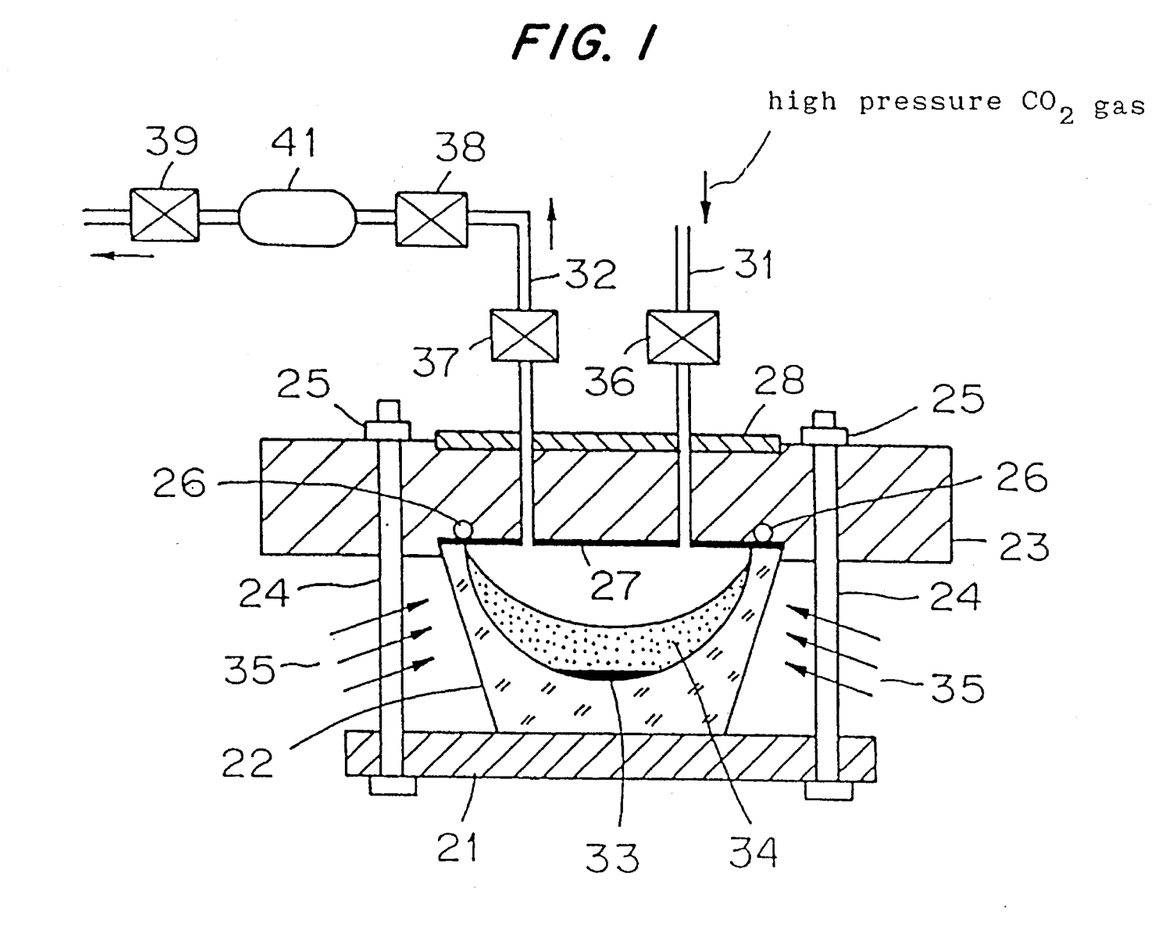
FIG. 1 is a cross-sectional view of a laboratory equipment for carrying out photoreaction using high pressure carbon dioxide according to the process of the present invention.

A laboratory equipment for practicing the process of the present invention is shown in FIG. 1. A vessel 22 made of fused quartz glass 22 is mounted on a base plate 21 of stainless steel. A top cover plate 23 of stainless steel closes the top opening of the vessel 22 and is fastened to the base plate 21 by bolts 24 passed through the cover and base plates and nuts 25 tightened onto the bolts to clamp the vessel 22 between the cover and base plates. An O-ring seal 26 is interposed between the top end of the vessel and the cover plate 23 to hermetically seal the vessel from the exterior. The undersurface of the cover plate 23 facing the top opening of the vessel 22 is lined with Au layer to prevent the stainless steel material of which the cover plate is formed from affecting the chemical reaction.

A heater 28 is mounted on the upper surface of the cover plate 23. Pipes 31 and 32 communicating with the vessel extend upwardly through the cover plate 23 and heater 28. Water 33 and powder of metallic oxide 34 are contained in the vessel 22. The powder of metallic oxide 34 which may be employed may include ZnO powder, WO₃ (tungsten oxide) powder, and a mixture of them, ZnO powder having CuO (copper oxide) mixed therein, and the like. A few cc of the water 33 and 2 to 5 g of the metallic oxide powder 34 were charged into the vessel 22. The powder had a surface area of about 10 m³/g. The metallic oxide powder 34 was subjected to heat treatment for surface activation prior to being charged into the vessel 22. The activation treatment was effected by heating at 400° C. for 4 hours in the case of ZnO powder and at 600° C. for 5 hours in the case of $WO_3$ powder, under vacuum in both cases. The constituents of the impurity build-up on the surface of the ZnO powder were analyzed for elements by using Auger spectroscopic analysis. The results are shown in the following table:

| Elements | Zn | O | C | S | P | Si |
| --- | --- | --- | --- | --- | --- | --- |
| Before heat treatment | 38.0 | 46.7 | 4.7 | 0.0 | 2.5 | 8.1 |
| After heat treatment | 37.6 | 50.4 | 0.0 | 0.9 | 3.2 | 7.8 |

It is seen from this analysis that upon the ZnO powder being subjected to heat treatment, the sulfur S and phosphorus P among the impurities in the powder will rise up to the surface region to constitute the impurity level. The silicon Si will migrate from the wall of the vessel 22 into the ZnO.

As a visible light source, light from a 75 W xenon lamp (not shown) was used with the ultraviolet light cut off by a filter to irradiate the metallic oxide powder 34 in the vessel 22 with visible light 35 from the peripheral side of the vessel. The entire vessel 22 was cooled to 5° C., and a cylinder (not shown) of liquified carbon dioxide gas (55 atm) was connected to the pipe 31 and a valve 36 associated with the pipe 31 was opened to introduce high pressure carbon dioxide gas into the vessel 22 up to a pressure of 30 to 40 atm.

The pressure in the vessel 22 was then gradually reduced to 0.1 atm through valves 37, 38 and 39 and a pressure regulator 41 disposed in the pipe 32, whereupon the products were removed from the vessel 22 and analyzed by a quadrupole mass spectrometer.

Figure 2:
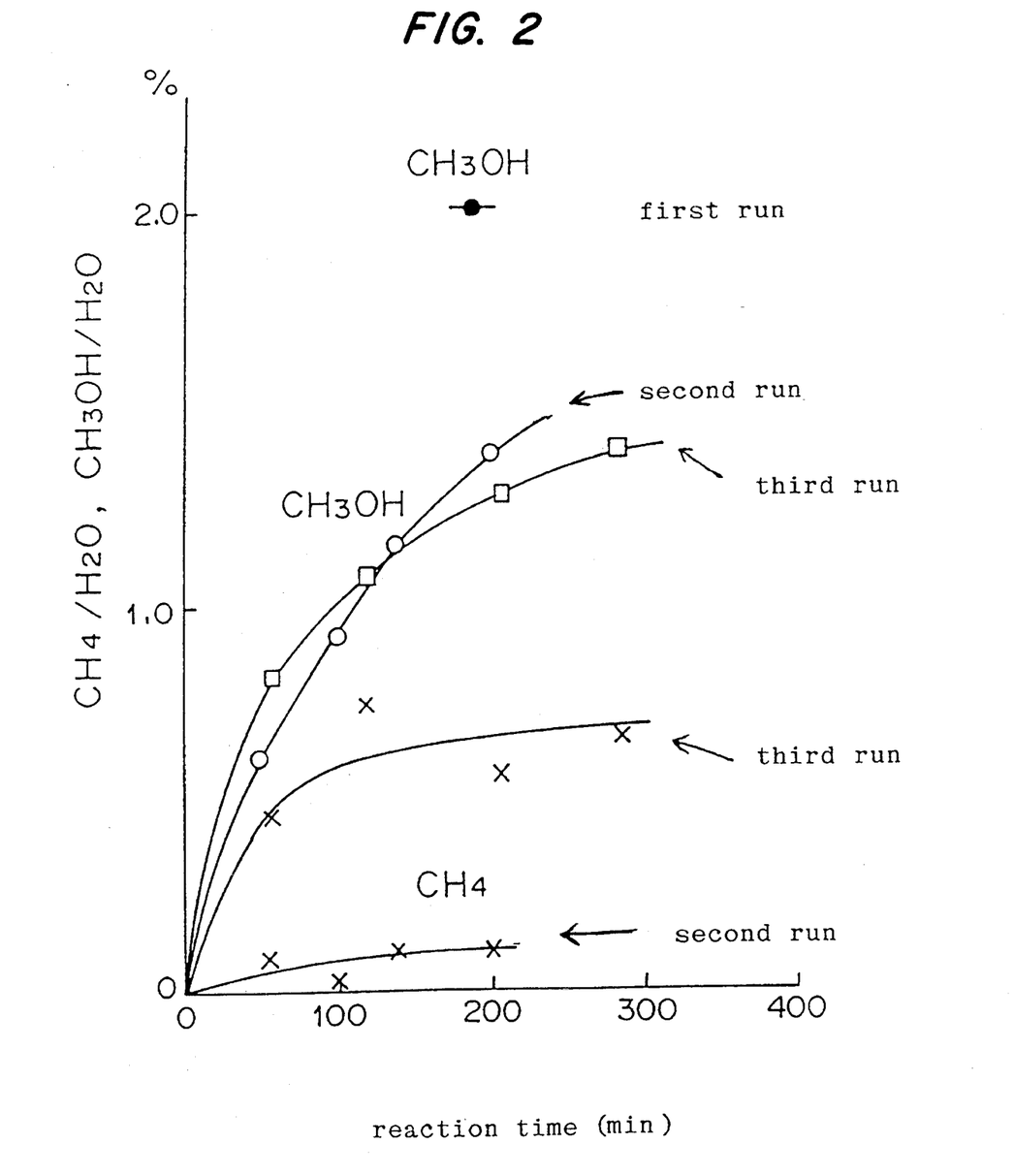
FIG. 2 is a diagram showing the production of organic substances using irradiation by visible light.

FIG. 2 shows the ratios of the organic substances relative to $H_2O$, the organic substances being produced using irradiation by visible light in the clathrate hydrate phase at 5° 1 C. and under the $CO_2$ atmosphere at 33 atm. The abscissa of the graph represents the reaction time (min). The ZnO powder was brought into contact with saturated water vapor at 1 atm prior to being subjected to a high pressure.

In the second and following test runs, after ZnO used in the preceding run was restored to the normal temperature and pressure, water and carbon dioxide gas were supplied to place the ZnO under the conditions of 5° C. and 33 atm without heat treating it, prior to the test.

In the first test run, as much as 2% of methanol $CH_3OH$ was produced. With an increase in the number of tests repeated, the amount of methanol produced correspondingly decreases whereas that of methane $CH_4$ produced increases.

Figure 3A:
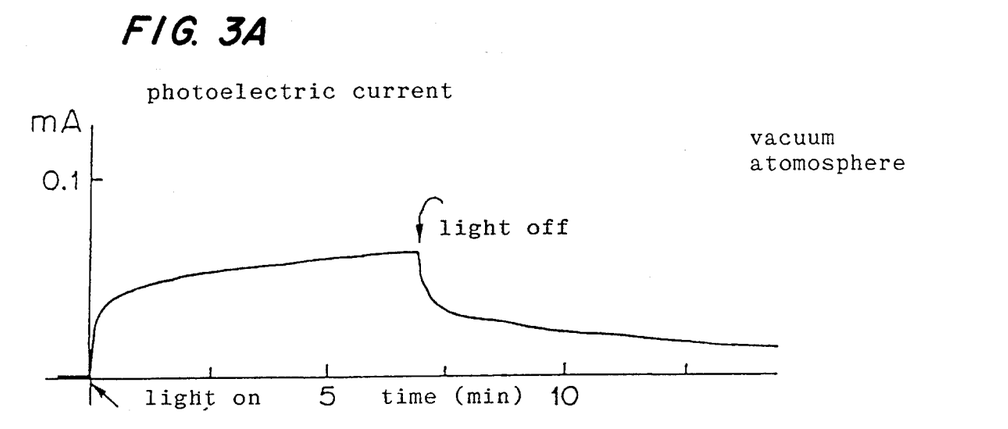
FIG. 3A is a diagram showing the excitation of photoelectric current in the surface of ZnO (10$\bar{1}$0) and its effects on the surface chemical reaction in the case where irradiation by monochromatic light is applied under vacuum.
Figure 3B:
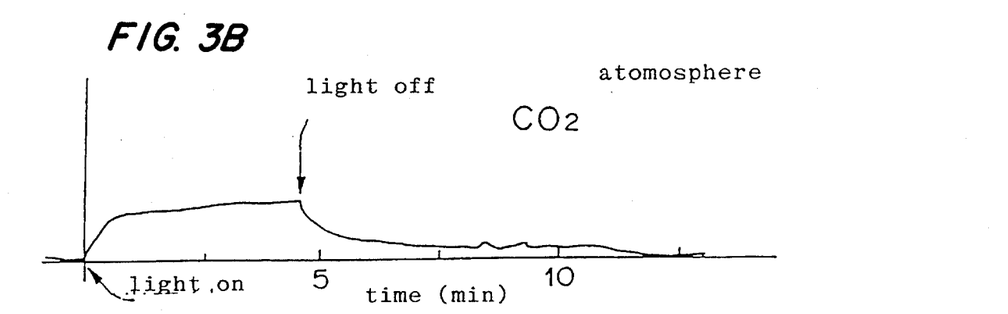
FIG. 3B is a diagram showing the excitation of photoelectric current on the surface of ZnO (10$\bar{1}$0) and its effects on the surface chemical reaction in the case where irradiation by monochromatic light is applied in a CO₂ gas atmosphere.
Figure 3C:
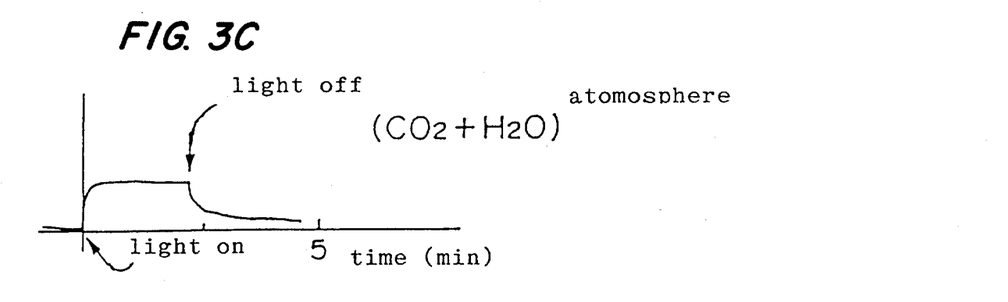
FIG. 3C is a diagram showing the excitation of photoelectric current in the surface of ZnO (10$\bar{1}$0) and its effects on the surface chemical reaction in the case where irradiation by monochromatic light is applied in an atmosphere of CO₂ gas and H₂O gas.

Next will be shown the experiments substantiating that photoelectric current is induced by visible light across ZnO, and that the photoelectric current contributes to photoreaction to produce organic substances. Electron and hole excitations are caused in the surface of ZnO single crystal (10 10) by visible light whereby photoelectric current is induced in the crystal surface. FIGS. 3A, 3B and 3C show the magnitude of photoelectric currents as induced by irradiating the ZnO single crystal surface with monochromatic light at $\lambda$=397 nm (E=3.1 eV) (A) in a vacuum atmosphere, (B) in a $CO_2$ gas atmosphere at 120 Torr, and (C) in an atmosphere of $CO_2$ gas at 120 Torr and $H_2O$ gas at 20 Torr, respectively. A relatively large photoelectric current occurs under vacuum whereas the photoelectric currents are reduced in the atmospheres of $CO_2$ gas and $CO_2/H_2O$ gases. It is to be understood that the decrease in the photoelectric current corresponds to that portion of the current consumed in the decomposing reaction of $CO_2$ and $H_2O$.

Figure 4:
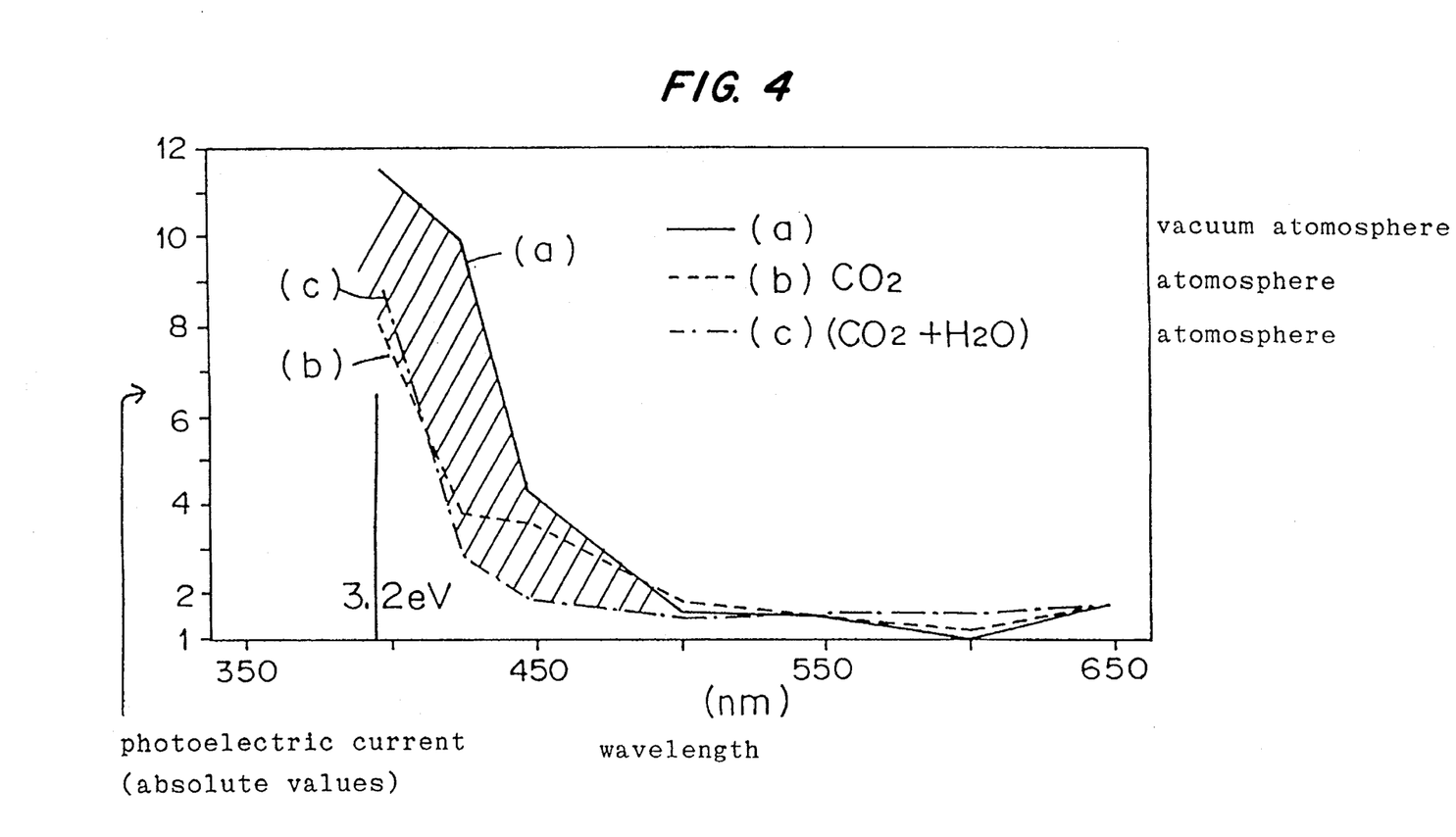
FIG. 4 is a diagram showing the dependency of the surface photoconductance on the wavelength of irradiation light and the decrease in photoelectric current due to the surface chemical reaction.

FIG. 4 shows the experiments similar to those of FIGS. 3A–3C but conducted with irradiation lights having different wavelengths. It is seen from this graph that the induction of the surface photoelectric current is caused mainly by light having a wavelength shorter than about 500 nm. The crosshatched areas in the FIG. 4 graph represent the photoelectric current consumed in the surface reaction of $CO_2$ and $H_2O$ with the aid of visible light.

Figure 5:
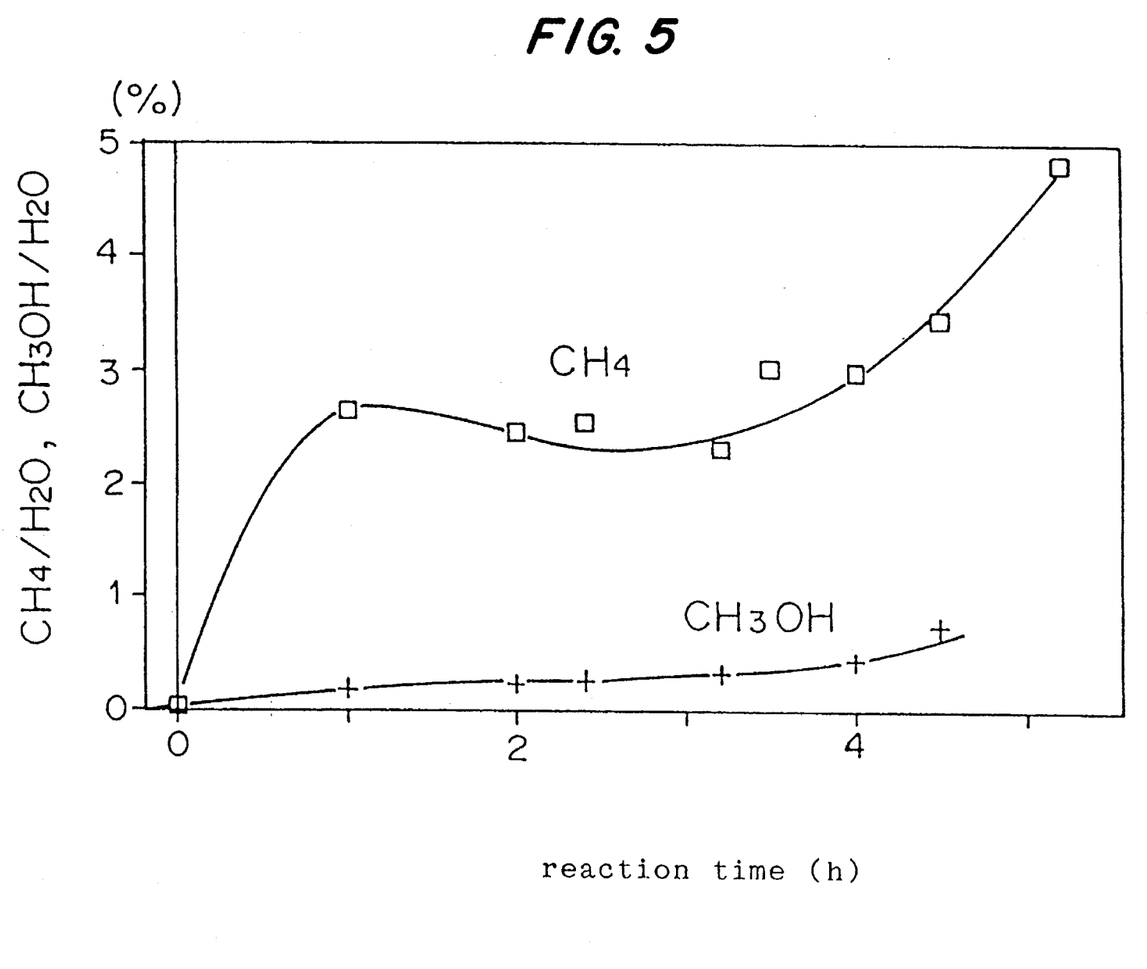
FIG. 5 is a diagram showing the products of photoreaction by the agency of fine particles of ZnO suspended in water at 5° C. and 33 atm of CO₂.

FIG. 5 shows the products as produced on ZnO powder while being immersed, that is, suspended in pure water at 20° C. and 1 atm by irradiating the ZnO powder with visible light under the conditions of 5° C. and 33 atm in which a clathrate hydrate phase is generated. In this case, methane is predominantly produced with very little production of methanol.

Figure 6:
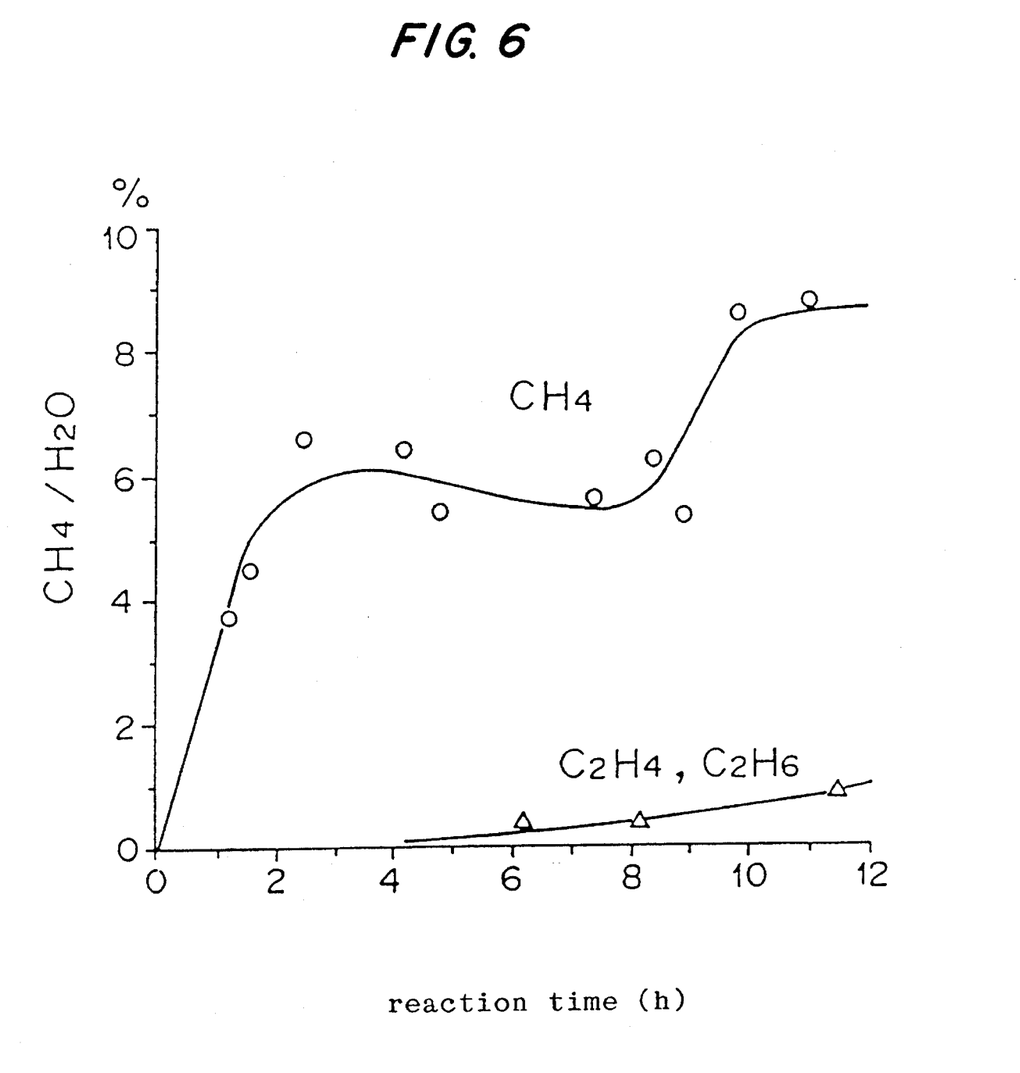
FIG. 6 is a diagram showing the products of photoreaction by the agency of ZnO having CuO mixed therein.

FIG. 6 shows the products as produced on the metallic oxide powder 34 comprising ZnO powder having 0.5 weight % of CuO powder mixed therein while being suspended in water by irradiating the metallic oxide powder with visible light under the clathrate-hydrate-phase-forming conditions of 5° C. and 33 atm. In this example, methane is a main product with small amounts of ethylene and ethane.

As described hereinabove, according to this invention, water and carbon dioxide are applied to surface activated metallic oxide under the conditions in which a clathrate hydrate phase is formed, or alternatively a clathrate hydrate phase is brought into contact with the surface of surface activated metallic oxide, and carbon dioxide is applied to the surface activated metallic oxide, whereby it is possible to convert carbon dioxide to organic substance with 50 to 100 times as high efficiency as that achievable by the prior art.

A high pressure of 30 to 40 atm is needed to form a clathrate hydrate phase. However, the carbon dioxide contained in exhaust gases as collected from stacks is usually contained as liquified carbon dioxide in cylinders at a pressure of 55 atm. Carbon dioxide gas may be thus supplied at a reduced pressure of 30 to 40 atm from such cylinders, so that no special facilities are required to pressurize carbon dioxide gas.

Especially, if the arrangement is made such that carbon dioxide gas is converted to methanol, it may be used not only for industrial raw material but also as automobile fuel as an additive to gasoline.

The temperature control need not be precise. If the temperature is set at about 5° C., temperature fluctuations on the order of ±3° C. would not deviate the temperature from the clathrate-hydrate-phase-forming conditions. If the temperature is below 0° C., the water will be frozen, so that it will take long to form a clathrate hydrate phase.

I claim:

1. A photochemical method for converting carbon dioxide gas to an organic substance, comprising the steps of:

(a) heating metallic oxide particles to activate the surfaces thereof, (b) forming a clathrate hydrate phase of water in contact with the surface activated metallic oxide particles, (c) introducing carbon dioxide gas into the clathrate hydrate phase, and (d) irradiating the surface activated metallic oxide particles with visible light and converting the carbon dioxide gas to the organic substance.

2. The method according to claim 1, wherein the clathrate hydrate phase is formed at a temperature of 0° to 10° C. and a pressure of 30 to 40 atm.

3. The method according to claim 1, wherein said metallic oxide particles comprise particles of ZnO.

4. The method according to claim 1, wherein said metallic oxide particles comprise particles of $WO_3$.

* * * * *

UNITED STATES PATENT AND TRADEMARK OFFICE
CERTIFICATE OF CORRECTION

PATENT NO. : 5,482,599
DATED : January 9, 1996
INVENTOR(S) : Masao WATANABE

It is certified that error appears in the above-indentified patent and that said Letters Patent is hereby corrected as shown below:

Column 1, line 5, before "FIELD OF THE INVENTION" insert –BACKGROUND OF THE INVENTION–; and line 17, delete "researches' and insert –research–.

Column 5, line 44, delete "5°]" and insert –5°– therein.

Signed and Sealed this

Fourth Day of June, 1996

*Attest:*

BRUCE LEHMAN

*Attesting Officer*  *Commissioner of Patents and Trademarks*